United States Patent [19]

Norris

[11] 4,429,576

[45] Feb. 7, 1984

[54] ULTRASONIC INSPECTION APPARATUS

[75] Inventor: James R. Norris, New Fairfield, Conn.

[73] Assignee: Dapco Industries, Inc., Ridgefield, Conn.

[21] Appl. No.: 289,209

[22] Filed: Aug. 3, 1981

[51] Int. Cl.³ .............................................. G01N 29/04
[52] U.S. Cl. ..................................... 73/636; 73/624; 73/627; 73/609
[58] Field of Search ................. 73/636, 627, 622, 624, 73/609

[56] References Cited

U.S. PATENT DOCUMENTS

| | | | |
|---|---|---|---|
| 3,135,109 | 6/1964 | Werner | 73/625 |
| 3,251,220 | 5/1966 | Joy | 73/614 |
| 3,287,963 | 11/1966 | Stanya et al. | 73/614 |
| 3,354,700 | 11/1967 | Schindler | 73/616 |
| 3,415,110 | 12/1968 | Cowan | 73/628 |
| 4,004,455 | 1/1977 | McKee et al. | 73/615 |
| 4,174,636 | 11/1979 | Pagano | 73/636 |

Primary Examiner—Howard A. Birmiel
Attorney, Agent, or Firm—Fitzpatrick, Cella, Harper & Scinto

[57] ABSTRACT

An ultrasonic inspection apparatus for inspecting a test piece includes an ultrasonic transducer for transmitting test signals into the test piece, for receiving associated response signals reflected back thereto, and for generating a defect signal when a response signal indicates an abnormal condition in the test piece. A control signal generator generates a control signal at predetermined intervals of distance of movement of the transducer relative to the test piece while the transducer generates test signals at a frequency independent the control signal frequency. A principal counter counts the control signals and generates an alarm signal when its count exceeds a value indicating that sufficient defect signals have been generated during movement of the transducer over a predetermined distance to confirm the presence of an unacceptable abnormal condition. A reset counter is connected to the control signal generator for also counting the control signals, is connected to the transducer for receiving defect signals therefrom, and is connected to the principal counter for generating a reset signal therefor. The reset counter is reset by each of the defect signals and generates one reset signal when its count exceeds a predetermined amount indicative of the maximum distance of movement of the transducer during which a defect signal may not be generated from an unacceptable abnormal condition.

19 Claims, 4 Drawing Figures

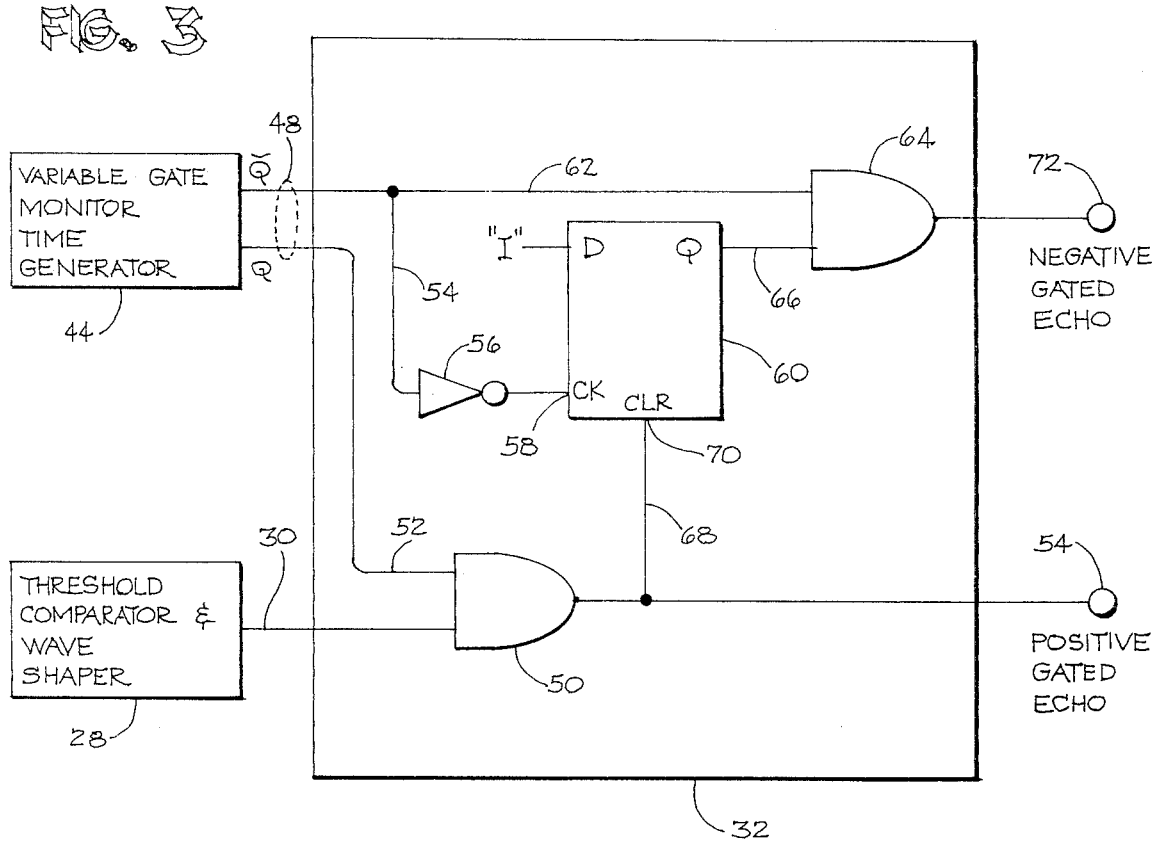

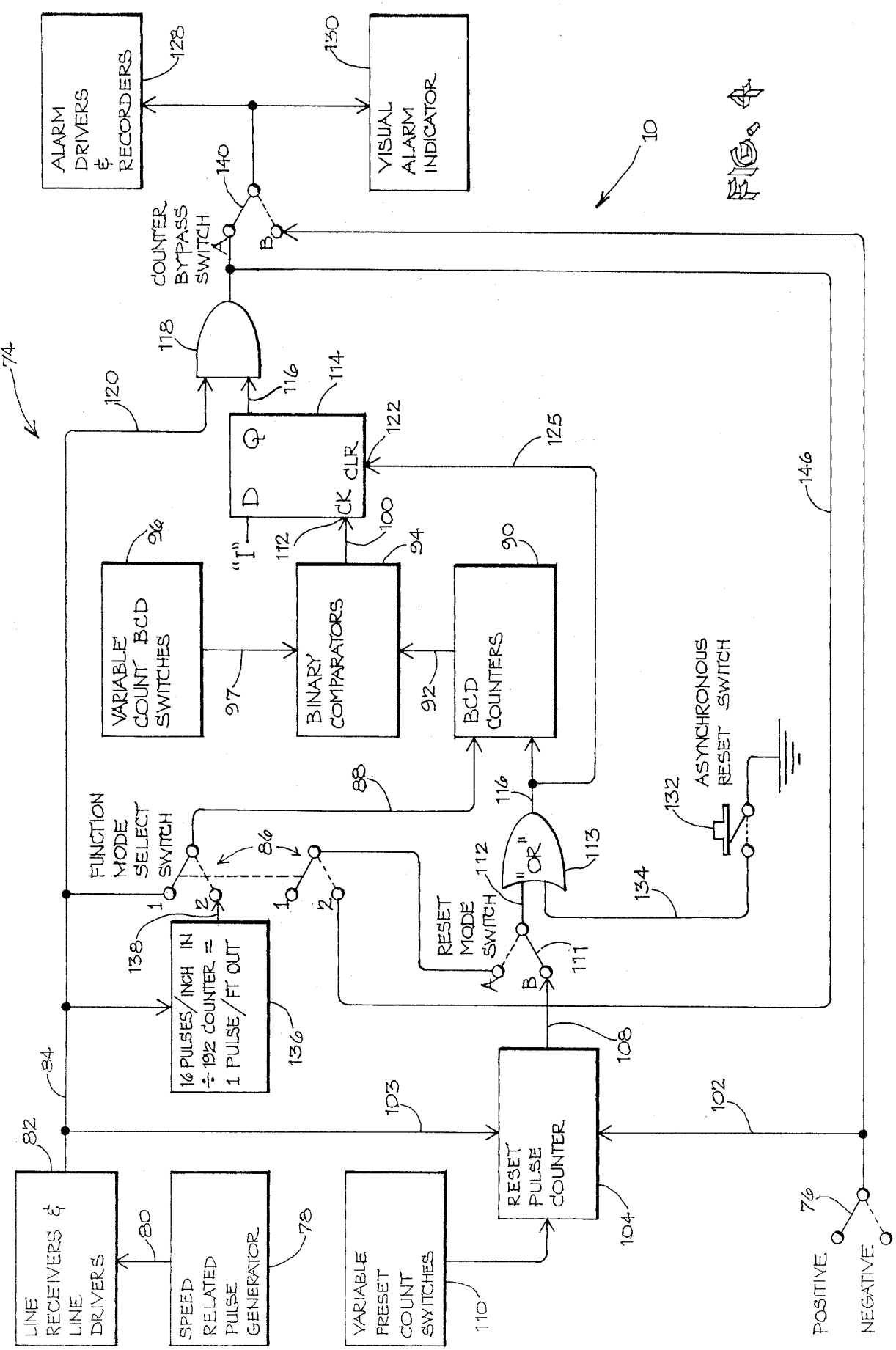

ULTRASONIC INSPECTION APPARATUS

BACKGROUND OF THE INVENTION

1. Field of the Invention

The present invention relates generally to an ultrasonic inspection apparatus for nondestructively inspecting an object such as, for example, a railroad rail. The principles of the present invention may, nevertheless, be incorporated in any testing apparatus in which an object is probed with sequentially generated signals, be they ultrasonic or other types of energy, capable of indicating the presence of a flaw or defect in the test piece.

In recent years, various developments have been made in apparatus and methods for automatically and rapidly inspecting a solid test piece such as a railroad rail. Such developments have been brought on by the need to provide fast, automatic, and reliable inspections that can be conducted economically, yet which permit appropriate maintenance to assure a high degree of safety in operation of rolling stock over such rail.

The developments in ultrasonic and in other nondestructive testing may, of course, be used to inspect objects other than railroad rails with equal advantage.

As further background, it should be noted that some flaws or defects (hereinafter also referred to as "abnormal conditions") are acceptable. For example, abnormal conditions smaller than a certain minimum size may be tolerated in the test piece. Furthermore, certain abnormal conditions result from intentional modification of the test piece and, therefore, are tolerable. For example, a bolt hole in a railroad rail is an abnormality but one that is expected and acceptable. It is desirable that test equipment reliably detect unacceptable abnormal conditions and, within this criterion, not signal a defect when a tolerable abnormal condition is indicated.

2. Description of the Prior Art

Various apparatus have been proposed in the past for performing ultrasonic inspection of test pieces and for analyzing the data generated by the inspection. Such apparatus operate by electrically pulsing an ultrasonic transducer or plurality of transducers to direct a high frequency sound wave or waves into the test piece. Such sound waves are transmitted through the test piece and may be reflected back to the transducer either by an expected or abnormal condition. Upon receipt of the reflected sound wave the transducer is again energized to generate a response signal. Thus, a defect in the test piece may be indicated by receipt of reflected energy from an abnormal condition, that is, receipt of reflected energy at a time after initial propagation of the wave indicating the presence of a condition which should not exist, or by failure to receive reflected energy from an expected condition within an expected time period.

U.S. Pat. Nos. 4,174,636 (Pagano) and 4,165,648 (Pagano) each disclose a two wheel ultrasonic rail testing system. Each wheel carries a plurality of ultrasonic transducers for probing an object such as a railroad rail with energy propagated at ninety degrees to the surface of the rail and forwardly and rearwardly from the wheel. Further ultrasonic transducers are provided for probing opposing gage and field corners of the head of the railroad rail. Because of the multiplicity of the ultrasonic transducers placed in each wheel to propagate energy at various angles in the rail, a wide variety of defects may be detected.

U.S. Pat. No. 3,415,110 (Cowan) discloses an ultrasonic inspection apparatus which includes a plurality of ultrasonic transducers oriented to probe various areas of a rail and which includes apparatus for processing defect signals generated by such transducers to indicate the presence of an unacceptable abnormal condition. More particularly, this system includes circuitry coupled to each differently oriented transducer for pulsing it each time it is moved by a predetermined distance relative to the rail. The response signals or echoes returned to one transducer that indicate a defect are counted and if this count exceeds a predetermined number indicative of an unacceptable abnormal condition an alarm signal is generated. This first counter is coupled to and reset by a second counter coupled to another of the transducers. Accordingly, indication of an unacceptable abnormal condition is dependent upon particular responses from two transducers. It is claimed that the multiplicity of counters prevent the apparatus from generating an alarm from separate acceptable targets or conditions but nevertheless causes generation of an alarm from an unacceptable target or condition that is so shaped as not to reflect ultrasonic energy from all parts.

The apparatus of the Cowan patent is, however, characterized by certain drawbacks. Because each transducer is pulsed at a frequency that is a function of its rate of movement relative to the test piece, non-uniform ultrasonic energy levels may be generated. Further, since the rate at which the ultrasonic transducers are pulsed varies with their speed over the test piece, it may be difficult to correlate pulsing of differently oriented transducers so as to minimize generation of unwanted ultrasonic noise. And, this system is relatively complicated in that responses from more than one transducer which are oriented differently are used to generate an alarm response.

U.S. Pat. No. 4,004,455 (McKee et al) discloses an improved and much simplified flaw detecting apparatus for railroad rails and the like. In this system a speed related pulse generator generates pulses at a frequency that is a function of the speed of the test vehicle which, therefore, is directly related to the distance traveled by the vehicle. This speed related pulse generator is coupled to a counter which counts the speed related pulses. An ultrasonic transducer is pulsed by a free running pulse generator at a fixed rate independent of the speed of the vehicle or the distance traveled by the vehicle. The free running pulse generator operates completely independently of the speed related speed pulse generator. The free running pulse generator is also coupled through a delay to a NAND gate having a second input from the ultrasonic transducer. The delay introduced in the output pulses generated by the free running pulse generator is equal to the time expected from generation of an ultrasonic wave propagated into the rail to return of that wave from a known target such as the bottom of the rail from which the transducer generates an expected response signal. Accordingly, if an ultrasonic response signal is received by the transducer within the expected time, both inputs to the NAND gate are satisfied.

The output from the NAND gate is also connected to the counter. The counter is continuously reset as long as expected response signals are received. However, in the absence of an expected response signal, the inputs to the NAND gate are not satisfied since the input from the delay will be received at a different time than that from the transducer circuitry. Failure of the NAND gate to be satisfied is an indication of a defect. Accordingly, as long as a defect indication is yielded, the counter is permitted to accumulate counts indicative of distance traveled. When the count accumulated by the counter exceeds a predetermined amount, indicative of length of an abnormal condition which is unacceptable, an alarm signal is generated.

The McKee et al apparatus provides advantages over the Cowan apparatus since it is much simplified. Further, since the ultrasonic transducers are pulsed at a fixed rate independent of speed and distance traveled relative to the rail, the level of ultrasonic energy generated may be carefully and precisely controlled. The McKee et al, apparatus is, however, still characterized by certain drawbacks. More particularly, it is specifically designed to indicate defects by absence or untimely receipt of an expected response signal by the transducer. It does not contemplate detection of defects simply by receipt of unexpected response signals. Further, if a defect is unacceptably long yet fails to create loss of a rail bottom response signal during some portion thereof, the counter may be reset to prevent generation of an alarm signal when one otherwise should be generated. Therefore, as disclosed, it is possible that an alarm signal will fail to be generated even from an unacceptable abnormal condition.

Still other ultrasonic inspection apparatus are disclosed in U.S. Pat. Nos. 2,736,193 (Van Valkenburg et al); 3,287,963 (Stanya et al); 3,354,700 (Schindler); 2,875,607 (Boxcer et al); 3,041,872 (Brown et al); 3,135,109 (Werner); 3,233,450 (Fry); 3,251,220 (Joy); 3,260,105 (McNulty); and 3,048,031 (Beaujard et al).

SUMMARY OF THE INVENTION

It is an object of the present invention to provide an apparatus and system to non-destructively inspect a test piece in order to and signal abnormal conditions therein.

More particularly, it is an object of the present invention to incorporate the desirable features of certain known systems yet to enhance the accuracy and reliability with which unacceptable abnormal conditions are detected and indicated by eliminating or minimizing the principal drawbacks in such known apparatus.

Accordingly, it is a principal object of the present invention to provide a system for non-destructively inspecting a test piece that includes at least one test signal transmitting and receiving device such as an ultrasonic transducer which is operated or pulsed at a known fixed frequency independent of movement of the transmitting and receiving device relative to the test piece. Therefore, if the device is an ultrasonic transducer, the level of ultrasonic energy generated may be carefully controlled. Further, if more than one transducer are incorporated in the inspection apparatus, the sequence in which such transducers are pulsed may be carefully and precisely set to minimize undesirable noise.

It is a further object of the present invention to provide an inspection apparatus that reliably indicates the presence of an unacceptable and a particularly long or extensive abnormal condition which may not uniformly produce defect signals. More particularly, it is an object of this invention to provide an inspection apparatus that reliably signals the presence of a long or extensive abnormal condition that might, nevertheless, fair to produce defect signals over some portion of its extent.

It is still another object of the present invention to provide an inspection apparatus in which each ultrasonic transducer or each plurality of transducers oriented in the same fashion can be actuated to reveal the presence of an abnormal condition that fails to produce uniform defect signals.

It is yet another object of the present invention to provide an inspection apparatus that generates an alarm indicative of the magnitude of an unacceptable abnormal condition rather than one indicative of the mere presence of such a condition.

Another object of the present invention is to provide an inspection apparatus that has the ability to test for unacceptable abnormal conditions which are revealed both by the failure of an ultrasonic transducer to receive an expected response signal or by the receipt by the ultrasonic transducer of an unexpected response signal.

In general accordance with the present invention, the apparatus for inspecting a test piece and indicating an unacceptable condition therein includes a device, such as a ultrasonic transducer, for transmitting a test signal into the test piece, for receiving an associated response signal reflected back to the device, and for generating a defect signal when the character of the response signal indicates an unexpected condition in the test piece. For example, this response signal character may be absence of a response signal from a known feature of the test piece such as a rail bottom, or may be presence of a response signal reflected from unexpected condition such as a crack in the rail.

The apparatus further includes a vehicle or other means for moving the transmitting-receiving device relative to the test piece. A control signal generator generates a control signal at each of a plurality of predetermined intervals of distance of movement of the transmitting-receiving device relative to the test piece, that is, as a function of the speed of the vehicle. A free running pulse generator or triggering device pulses the transmitting-receiving device to sequentially generate test signals at a frequency independent of generation of the control signals. A resettable principal counter counts the control signals in response to generation of defect signals and is reset to an initial valve in the absence of generation of defect signals. The principal counter generates an alarm signal when its count of control signals exceeds a predetermined amount in response to generation of sufficient defect signals movement of the ultrasonic transducer over a predetermined distance to confirm the presence of an abnormal condition that is unacceptable.

In general accordance with the present invention, the apparatus further includes the improvement comprising a reset pulse counter connected to the ultrasonic transducer for receiving defect signals therefrom. The reset counter is also connected to the control signal generator and is reset to an initial amount upon receipt of a defect signal but counts control signals in the absence of receipt of defect signals and produces a reset signal when the accumulated count equals a predetermined amount indicative of the maximum distance of movement of the transducer during which a defect signal may not be produced from an unacceptable abnormal condition. The reset counter is further connected to the principal counter for conducting a reset signal thereto. Accordingly, the principal counter is reset by the reset signal when the reset counter accumulates a count equal to the predetermined amount indicating that defect signals have been generated during movement of the transducer over a distance exceeding the maximum distance. However, the principal counter does accumulate a count of control signals as long as the reset counter receives at least one defect signal before accumulating a count exceeding the predetermined amount.

In further general accordance with the present invention, the apparatus for inspecting a test piece also includes a system for determining the distance of movement of the ultrasonic transducer relative to the test piece between generation of an alarm signal and resetting of the principal counter. This distance, added to the predetermined distance over which defect signals must be received to confirm the presence of an unacceptable abnormal condition, is a measure of the total length or magnitude of the unacceptable abnormal condition. This distance determining circuitry includes a flip-flop that is activated when one alarm signal is generated and de-activated when a reset signal is generated by the reset pulse counter.

Accordingly, the present invention provides substantial improvement over prior art inspection apparatus, such as apparatus that utilize ultrasonic transducers, in that each ultrasonic transducer may be used to detect an unacceptable abnormal condition in a test piece and reliably does so even though such condition may fail to produce defect signals from a portion thereof. Further, rather than merely sounding an alarm when an unacceptable condition is indicated, the inspection apparatus of the present invention also yields a direct indication of the magnitude of such a condition.

The apparatus of the present condition is also "universal" in nature in that it can both test for abnormal conditions indicated by failure of the ultrasonic transducer to receive expected response signals and receipt of the transducer of unexpected response signals.

These advantages are achieved in a system that operates its transmitting-receiving devices such as ultrasonic transducers at a fixed rate independent of vehicle speed, so that the prior substantial improvements in the control of ultrasonic energy levels and minimization unwanted noise are also achieved.

These and other objects, aspects, and features of the present invention will be pointed out in or will be understood from the following detailed description provided below in conjunction with the accompanying drawings.

BRIEF DESCRIPTION OF THE DRAWINGS

FIG. 3 is a schematic diagram of a gated positive and negative echo pulse generator that selectably produces a defect signal when the transmitting receiving device fails to receive an expected response signal or when this device receives an unexpected response signal.

FIG. 4 is a schematic block diagram of the components of this apparatus for processing defect signals and generating an alarm signal when an unacceptable abnormal condition is encountered.

DETAILED DESCRIPTION OF PREFERRED EMBODIMENTS

Figure 1:
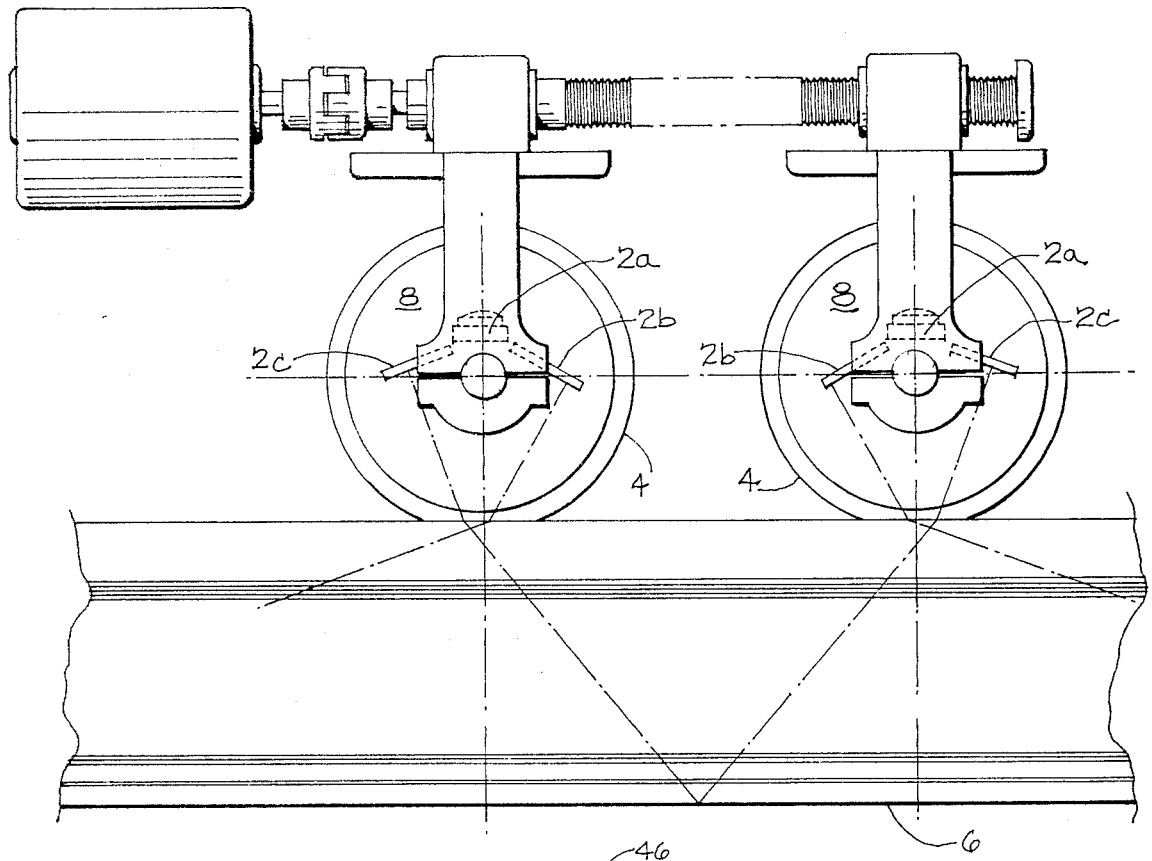
FIG. 1 is a side elevational view of a two wheel ultrasonic inspection device with which the apparatus of the present invention may be incorporated.

The inspection apparatus of the present invention may be adapted for many applications in which it is desirable to non-destructively probe a test piece. However, for convenience the illustrative embodiment described in the present specification is an apparatus designed particularly to inspect a railroad rail. For such an application the apparatus includes of a plurality of ultrasonic transducers 2 mounted in two test wheels 4 that make rolling, ultrasonically coupled contact with the top of a rail 6. The wheels may be moved along the rail by any suitable vehicle. U.S. Pat. Nos. 4,165,648 (Pagano) and 4,174,636 (Pagano) both disclose suitable test wheels and a vehicle in detail and the disclosures of these patents are incorporated herein by reference.

Each wheel 4 is filled with a coupling liquid 8. Accordingly, when an ultrasonic transducer is energized, high frequency sound waves or test signals are transmitted through the coupling liquid in the wheel into the rail. If the sound waves encounter a discontinuity in the rail, they will be reflected and depending upon the orientation of the discontinuity may be reflected back as an associated response signal to the transducer. Upon receipt of the reflected response signal, the transducer generates a signal indicating the response.

As explained in detail in the Pagano Patents mentioned above, the plurality of transducers incorporated in such test wheels are oriented so that a wide variety of areas in the rail may be effectively probed. Each transducer or set of similarly oriented transducers is referred to as a "channel". For example, one set of transducers 2a in each wheel is arranged to transmit ultrasonic energy into the rail at an angle of 90 degrees to the rail head and is called the "zero degree" channel. Each rail further has a set of extreme forward or backward looking transducers 2b each arranged to transmit ultrasonic energy into the rail at an angle of 30 degrees to the perpendicular to the rail head which produces a beam of ultrasonic energy at a resultant angle of about 70 degrees to the perpendicular. Further each wheel includes transducers 2c that are oriented to transmit a beam of ultrasonic energy into the rail to be reflected from the rail bottom back toward a corresponding transducer in the other wheel. These are so-called "pitchcatch" transducers. Further, the wheels are equipped with "side-looking" transducers (not shown) that probe opposite corners of the rail head. All told then, there are at least eight transducer channels which are monitored to determine the presence or absence of a defect or abnormal condition in the rail.

As an example, in the case of the zero degree channel transducers 2a, ultrasonic energy will ordinarily be propagated therefrom through the rail and reflected back thereto in a known period of time. In the Pagano apparatus, these transducers are used to measure the thickness of the rail to adjust automatically the spacing of the two wheels for proper operation of the "pitchcatch" channel. However, if the ultrasonic energy generated by the zero degree transducers 2a encounters an abnormal condition, the bottom response signal will either be lost or will return to the transducer 2a in a time less than that expected for a normal bottom response signal. Therefore, a defect (such an abnormal condition) may be indicated by the loss of the expected bottom response signal.

As a second example, ultrasonic energy propagated by the forward or rearward looking transducers 2b will not be reflected back to the transducer unless an abnormal condition is encountered. In such a case, a defect (or abnormal condition) is indicated by receipt of a response signal by the associated transducers.

For convenience of explanation, the apparatus of the present invention will be explained only with reference to the zero degree ultrasonic transducer channel 2a.

A complication arises in accurate and reliable detection of unacceptable abnormal conditions because rails now in widespread use are usually not homogenious or continuous. Therefore, discontinuities other than the rail bottom or unacceptable abnormal conditions may exist. For example, discrete lengths of rail in many railroads are held together by tie plates which are bolted directly to the rail by bolts passing through the rail web. The bolt holes through which such bolts are passed will produce a reflected response signal other than that normally produced from the rail bottom. However, because a normal bolt hole is an acceptable deviation from the norm or an acceptable abnormal condition, it is desirable that the system not register an alarm when such a hole is encountered. Therefore, as is known, the system of the present invention incorporates circuitry that, in most cases, prevents an alarm signal from being generated if a discontinuity having dimension the size of a bolt hole or smaller is encountered. However, circuitry known in the prior art for preventing false alarms from expected and acceptable rail discontinuities creates certain difficulties. For example, as briefly mentioned above, in the system described in U.S. Pat. No. 4,004,455 (McKee et al) unacceptability of any abnormal condition is determined by measuring the distance over which the condition occurs and comparing the measured distance with a known minimum distance indicative of an unacceptable abnormal condition. This minimum distance may be the diameter of a bolt hole. If the abnormal condition occurs over a distance less than this diameter it is presumed to be acceptable; if over a greater distance, unacceptable.

More particularly, a counter counts speed related signals generated at each of a plurality of predetermined intervals of distance of movement of an ultrasonic transducer relative to the test piece. As long as no defect or abnormal condition is indicated, the counter is continuously reset. However, when an abnormal condition is encountered, the counter is not reset and therefore can accumulate a count related to distance. As long as abnormal conditions continue to be indicated, the counter accumulates a count. When the count exceeds a predetermined number indicating that the abnormal condition is unacceptable, an alarm signal is generated. However, if an actual defect or unacceptable abnormal condition is encountered that nevertheless fails to generate defect indicating response signals for a portion of it, it is possible that the counter will count up to a value less than that which would cause generation of an alarm signal, be reset by the failure to generate defect indicating response signals, and then begin to count again when defect indicating response signals are again produced. Therefore, even though the actual abnormal condition is unacceptable, the system will fail to generate an alarm signal and such conditions will go undetected. Providing a remedy for this principal disadvantage of systems such as that disclosed in the McKee et al Patent in which long or extensive abnormal conditions may go undetected, is one of the principal objects of the present invention.

A second disadvantage of many known systems is that they are arranged to generate an alarm signal once an unacceptable abnormal condition is detected. However, such an alarm signal typically only indicates the presence of an unacceptable abnormal condition and does not indicate the magnitude of that condition. For example, in the system disclosed in the McKee et al Patent, once an alarm signal has been generated, a second alarm signal can only be generated if the counter is reset and it counts back to the minimum predetermined number or if it is not reset, counts through its counting capacity and counts from zero again to the predetermined number. Therefore, a very long single defect may be indicated as two separate defects spaced by a distance at least equal to that indicated by the maximum capacity of the counter. Further, small defects close together cannot be accurately distinguished from one another since there is no indication where one defect ends and the second begins. It is also principal purpose of the present invention to remedy this drawback in the prior art.

As also mentioned briefly above, is another principal object of the invention to provide a system "universal" in nature, that can detect unacceptable abnormal conditions that are indicated either by failure to produce an expected response from a test signal or by production of an unexpected response.

With the background provided above, the apparatus of the present invention will now be described in detail with reference to FIGS. 2 through 4. These figures illustrate the general system architecture for pulsing the ultrasonic transducers in any one transducer channel illustrated in FIG. 1, for processing response signals received by the one transducer channel, and for generating a defect signal when the character of such response signal indicates that an abnormal condition is present in the test piece. These figures further illustrate the system architecture for processing defect signals to generate an alarm signal when an abnormal condition is unacceptable and, therefore, constitutes a flaw.

Figure 2:
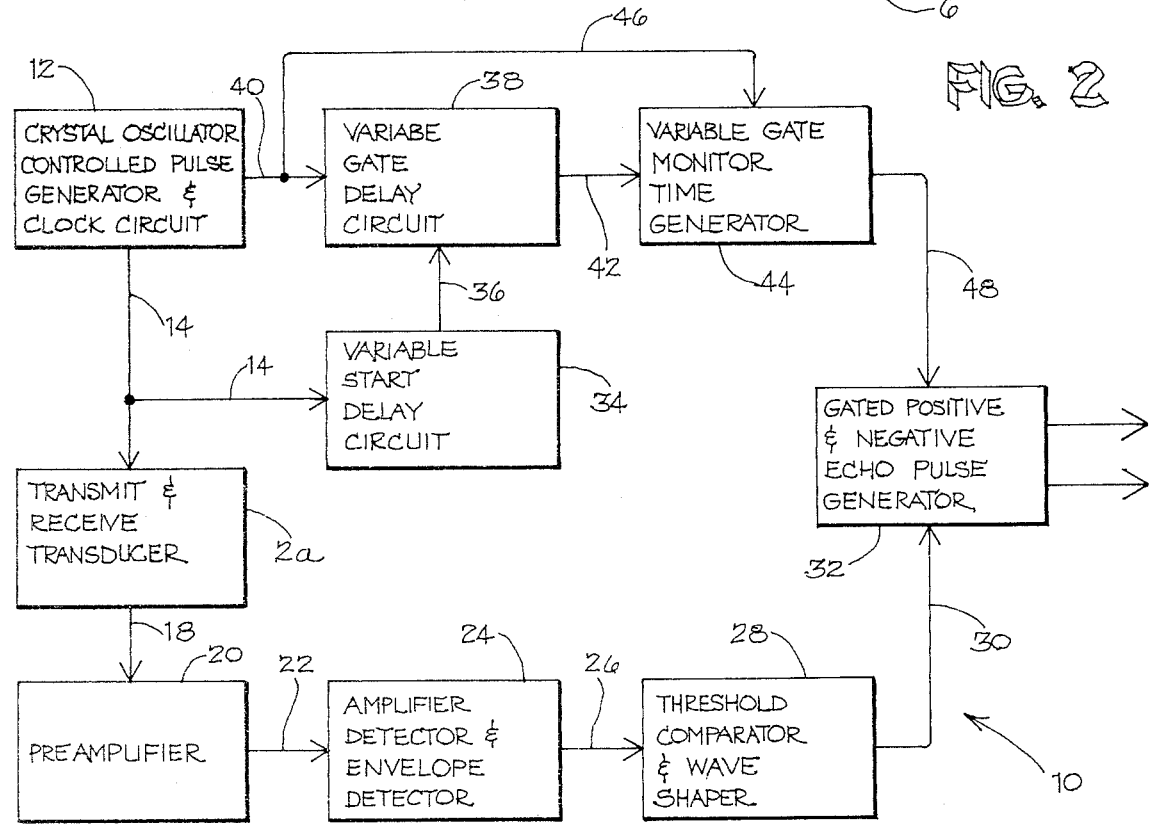
FIG. 2 is a schematic block diagram of the components of the present invention for generating defect signals indicative of unexpected conditions in a test piece inspected by this apparatus.

Referring first to FIG. 2, the portion of the apparatus, generally indicated at 10, for pulsing the ultrasonic transducers in any one transducer channel, assumed for convenience to be the zero degree channel, includes a crystal oscillator controlled pulse generator and clock circuit 12 that generates an output at a constant frequency of for example 800 Khz. This high frequency clock signal is internally reduced to a frequency of approximately 2 Khz and is conducted on line 14 to a transmitting and receiving device, namely the ultrasonic transducers in the zero channel 2a. The high frequency signal on the line 14 constitutes a trigger signal for the transducers 2a. The frequency of this trigger signal is chosen for most efficient operation of the transducers and for proper coordination of operation of one transducer channel with other transducer channels.

When the transducer 2a is pulsed, it generates a wave of ultrasonic energy that is conducted through the ultrasonic test wheel into the rail, encounters the bottom of the rail, and is reflected back to the transducer. Thereafter, the transducer will generate a response signal in response to the reflected energy that is conducted on line 18 to a preamplifier 20. From the preamplifier, the response signal is conducted on line 22 to an amplifier detector and envelope detector 24 that performs a full wave detection and envelope detection of the response signal. The now partially processed response signal is then conducted on line 26 to a threshold comparator and wave shaper 28 that discriminates between meaningful response signals and those that would result from, for example, background noise in the rail. The meaningful or significant response signals are then converted to discrete pulses by the threshold comparator and wave shaper 28 and are conducted on line 30 to a gated positive and negative echo pulse generator 32 that will be described in greater detail below.

The trigger signals on line 14 are also conducted to a variable start/delay circuit 34 which delays their transmission to subsequent circuitry to prevent generation of response signals during transmission of ultrasonic energy from the transducer 2a through regions not being tested. For example, the variable start/delay circuit 34 may be set to delay start of a test cycle unitl after the ultrasonic energy has been transmitted through the test wheel to the surface of the rail. The variable start/delay circuit generates a start pulse at a finite time after generation of the initial trigger signal on line 14 and conducts this start pulse on line 36 to a variable gate delay circuit 38. The variable gate delay circuit 38 is also connected on line 40 to the crystal oscillator controlled pulse generator and clock circuit 12 to receive the fixed 800 Khz clock signal generated thereby. This constant frequency clock signal constitutes a basic time reference from which further delays in gating periods may be calculated as will be described.

The variable gate delay circuit 38 generates a delayed gate pulse on line 42 at a finite time after receipt of a start pulse on line 36 to indicate the start of a gating peroid during which an actual test will be conducted. The gate start pulse on a line 42 is conducted to a variable gate monitor time generator 44 which also receives the clock signal from the crystal oscillator controlled pulse generator and clock circuit 12 on lines 40 and 46. The variable gate monitor time generator 44 sets the time at which a gate or test period, initiated by a gate start pulse from a variable gate delay circuit 38, ends. Accordingly, the variable gate delay circuit and variable gate monitor time generator determine the time after generation of a start pulse from the variable start-/delay circuit 34 of the start of a gate or test period and the duration of a gate or test period. The variable gate monitor time generator signals the gated positive and negative echo pulse generator on line 48 when the gate period begins and ends.

The circuitry described above permits different regions of the rail to be inspected. For example, if the zero degree transducer channel is being used to test for absence of bottom signal, the variable gate delay circuit 38 would be set to start a gate period at a time just prior to expected receipt by the transducer 2a of ultrasonic energy generated by it and reflected from the bottom of the rail back to it and the variable gate monitor time generator 44 would be set to end the gate period just after expected receipt of such ultrasonic energy reflected from the bottom of the rail. Accordingly, receipt of a response signal by the transducer 2a conducted through the treshold comparator and wave shaper 28 to the gated echo pulse generator 32 during this gate period would indicate an expected condition. Failure to receive such a response signal during the gate period may however, indicate an abnormal condition.

If it is desired to test the rail web region for presence of an abnormal condition, the variable gate delay circuit 38 and variable gate monitor time generator 44 would be set to begin a gate period at a time when response signal from the nearest defect in the web would be reflected to the transducer and to end at a time when the farthest defect in the web would reflect a response signal to the transducer.

Receipt of a response signal during the gate period in this case may indicate the presence of an abnormal condition. Failure to receive a response signal during this gate period would indicate that no abnormal condition exists.

As shown in greater detail in FIG. 3, the gated positive and negative echo pulse generator 32 is designed to selectably generate a defect signal either when an unexpected response signal is received or when an expected response signal is not received during a gate peroid. This receipt of an unexpected signal or failure to receive an expected response signal is that referred to herein as the "character" of the response signal that determines whether or not a defect signal is generated by the gated positive and negative echo pulse generator. More particularly, as can be seen there the variable gate monitor time generator 44 has two outputs, Q and $\overline{Q}$ which together constitute line 48. The gated positive and negative echo pulse generator 32 comprises a first AND gate 50 having one input from the Q output of the variable gate monitor time generator 44 and a second input on line 30 from the threshold comparator and wave shaper 28.

At the start of a gate period, that is with generation of a gate pulse from the variable gate delay circuit 38, and Q output of line 48 is enabled and the $\overline{Q}$ output is disabled. At the end of the gate period determined by the variable gate monitor time generator 44, the Q output therefrom becomes disabled and the $\overline{Q}$ output becomes enabled. Accordingly, during the gate period, one input 52 to the AND gate 50 is enabled. Therefore, upon receipt of a response signal on line 30, the other input to the AND gate 50 is also enabled, making both inputs enabled and generating a enabled output signal at the positive gated echo pole 54. The positive gated echo pole is used, then, when it is desirable to test for an abnormal condition indicated by receipt of an unexpected response signal during the gate period.

The $\overline{Q}$ output from the variable gate monitor time generator 44 is also connected on line 54 through an inverter 56 to the clock input 58 of a flip-flop 60.

The Q output is also connected on line 62 to one input of a second AND gate 64. The other input 66 to the AND gate 64 is from the Q output of the flip-flop 60. The output of the AND gate 50 is connected on line 68 to the clear input 70 of the flip-flop 60. The output from the AND gate 64 is connected to the negative gated echo pole 72 which is thus used in tests for an abnormal condition indicated by failure to receive expected response signals during a gate period. More particularly at the start of the gate period, the $\overline{Q}$ output of the variable gate time generator 44 becomes disabled but is inverted by the inverter 56, the output of which is connected to the clock input 58 of flip-flop 60 to become enabled. Accordingly, the flip-flop, which has a constantly enabled D input, is clocked at the start of the gate period so that the Q output thereof to AND gate 64 becomes enabled. However, the other input to the AND gate 64 on line 62 (the $\overline{Q}$ output from the variable gate monitor time generator) is disabled. Upon receipt of an expected signal, the output of AND gate 50 becomes enabled clearing input 70 of the flip-flop 60 to clear the Q output thereof on line 66. At the conclusion of the gate period, the Q output from the variable gate monitor time generator becomes disabled and the $\overline{Q}$ output becomes enabled. Accordingly, the input to the AND gate 64 on line 62 becomes enabled, the clock input to the flip-flop 60 remains disabled, and the Q output from the flip-flop on line 66 remains disabled. Therefore, receipt of an expected response signal results in the failure to produce a defect signal at the negative gated echo pole 72.

However, assume that the expected response signal is not received at the threshold comparator and wave shaper during the gate period for which a test is made. At the start of the gate period, the Q output of the variable gate monitor time generator 44 is enabled the $\overline{Q}$ output is disabled enabling the clock input 58 to the flip-flop 60. Therefore, the Q output therefrom on line 66 to the AND gate 64 becomes enabled. In the absence of a signal during the gate period, no output from the AND gate 50 will clear the flip-flop on line 68. Therefore, the output at Q remains enabled. At the conclusion of the gate period, the $\overline{Q}$ output from the variable gate monitor time generator becomes enabled and the output from the AND gate 64 similarly becomes enabled yielding a defect signal at the negative gated echo pole 72.

Accordingly, from the above description, it will be appreciated that the gated positive and negative echo pulse generator is capable of producing a defect signal (as described above an output enabled signal at the selected output pole 54 or 72), depending on the type of test being conducted when an expected response is not received or when an unexpected response is received. Accordingly, the apparatus of the present invention is "universal" in nature and provides great flexibility for conducting various types of tests with transducers having various orientations to probe different regions of a test piece.

The gated positive and negative echo pulse generator 32 is connected to further processing circuitry shown in FIG. 4 and forming a part of the apparatus 10, This circuitry, generally indicated at 74, is designed to detect unacceptable abnormal conditions reliably even if such unacceptable conditions fail to produce defect signals during portions thereof. More specifically this circuitry includes means for selectably coupling the positive and negative echo pulse generator 32 through either the negative gated echo pole 72 or the positive gated echo pole 54 thereto. As shown in FIG. 4 this means maybe a switch 76. This circuitry also comprises a speed related pulse generator 78 which may, for example, be a shaft encoder or tachometer that generates a control signal at each of a plurality of predetermined intervals of distance of movement of the ultrasonic transducers relative to the rail. For example, this generator 78 may generate a pulsating signal on line 80 of one pulse for every sixteenth inch of movement of the ultrasonic transducers 2. Of course, since the transducers are pulsed by the crystal oscillator controlled pulse generator and clock circuit 12, which runs freely at a constant frequency, pulsation of the transducers is completely independent of the speed related pulses generated on line 80 by the speed related pulse generator. Further, the speed related pulses vary in frequency depending upon the speed of movement of the transducers.

The speed related pulses are conducted on line 80 to a plurality of line drivers and line receivers 82 and from there are conducted on line 84 to a function mode select switch 86. When set in a first position, this switch conducts the speed related pulses on the line 88 to a binary coded decimal (BCD) counter 90 which is operable to count them sequentially. In the preferred embodiment, the counter is further able to count from 0 to 99 and reinitiate a second and subsequent counts at zero. The counter will accumulate a count of speed related signals unless reset in a matter described in greater detail below.

Generally, the BCD counter 90 is arranged to be reset in the absence of a defect signal from the gated positive and negative echo pulse generator 52 and to not be reset in the presence of such a signal.

The BCD counter is further connected on line 92 to a binary comparator 94 that is also connected to variable count binary coded decimal switches 96 on line 97.

The comparator 94 is arranged to yield an output enable or alarm signal on line 100 when the count accumulated in the counter 90 equals the count set in the variable count BCD switches 96. When the count in the counter 90 exceeds the count set in the switches 96, the output on line 100 from the comparator is disabled.

The variable count switches 96 are set at a number that indicates a distance of travel of the ultrasonic transducer relative to the rail at which an abnormal condition is considered unacceptable. They are also set to indicate a distance of travel greater than that during which defect signals may be generated by the gated positive and negative echo pulse generator from an expected condition, such as a bolt hole, that is acceptable. For example, if a test is being conducted with the zero degree transducer channel to inspect for an absence of the expected bottom signal, an abnormal condition may be indicated by a bolt hole. If the bolt hole is one half inch in diameter, defect signals will be produced for one half inch of transducer travel relative to the rail. Therefore, the variable BCD switches will be set at a number greater than eight so that an accumulated count in the BCD counter 90 of eight or less will not produce an output enable or alarm signal from the comparator on line 100.

As noted above, the system of the present invention and in particular the circuit 74 shown in FIG. 4 can minimize the chance of failing to indicate the presence of a long or extensive unacceptable abnormal condition which nevertheless fails to cause the inspection circuitry to produce defect signals during a portion of the inspection because, for example, of the orientation of some portion of the defect. More particularly, the gated positive and negative echo pulse generator is connected through switch 76 on line 102 to a reset pulse counter 104. Speed related pulses on line 84 are further conducted on line 103 to the reset pulse counter, which is also capable of counting the speed related pulses conducted thereto.

The reset pulse counter 104 is arranged to be preset with a predetermined number whenever a gated defect signal is received from the gated positive and negative echo pulse generator 32. In the absence of such a gated defect signal, the reset pulse counter 104 is permitted to count down from the predetermined amount. Further, the reset pulse counter is adapted to generate a reset signal on line 108 each time it counts down from the preset number to zero. The present number is set in the reset pulse counter by variable preset count switches 110 and equals a number that indicates a distance of travel during which defect signals may not be received from an abnormal condition which is nevertheless unacceptable. For example, a long or extensive abnormal condition, because of the orientation of at least some portion of it with respect to the probing ultrasonic energy, may fail to produce defect signals from that portion. However, the abnormal condition is nevertheless unacceptable. Therefore, as described further below, the reset counter prevents resetting of the BCD counter 90 if the abnormal condition fails to produce a defect signal during travel of the transducers over a distance equal to some arbitrary maximum distance. This arbitrary distance may be selected to be that during which the failure of the test piece to produce defect signals actually indicates the absence of an unacceptable abnormal condition. More particularly, a reset signal produced by the reset counter 104 is conducted on line 108 to a reset mode switch 111 which when set in position B conducts the reset signal on line 112 to an OR gate 113, which in turn conducts the reset signal on line 116 to the BCD counter 90. Accordingly, during an inspection, in the absence of indication of an abnormal condition from the circuitry of FIG. 2, the reset pulse counter will not be preset and will count down to zero. Upon counting down to zero, again in the absence of a defect indication, the reset pulse counter will generate a reset signal on line 108 through switch 111, OR gate 113 to the BCD counter each time it receives a speed related pulse. Thus, in the absence of a defect indication, the BCD counter 90 is continually reset after the reset counter has counted down to zero. Therefore, it does not accumulate a count such that an alarm condition will be indicated on line 100. However, at occurrence of a defect signal from the gated positive and negative echo pulse generator 32 the reset pulse counter will be preset and, therefore, will fail to generate a reset signal to the BCD counter 90 as described above. Accordingly, at each occurrence of a defect signal the BCD counter can accumulate a count of speed related pulses and if defect signals are generated during travel of the ultrasonic transducer over a sufficient distance of rail, an alarm condition will be indicated on line 100.

The reset counter is used as follows:

Assume that the variable count BCD switches 96 are set so that the binary comparator indicates an alarm on line 100 when the count of speed related pulses by the BCD counter 90 equals ten. That is, any condition from which a defect signal is generated for more than ⅝ inch is unacceptable. Assume further that it has been determined that defect signals may not be generated from such ⅝ inch abnormal condition for up to one quarter of an inch while the condition is nevertheless unacceptable. The variable preset count switches 110 are then set at four.

Prior to encounter of the abnormal condition, the reset pulse counter will not receive defect signals and therefore will count down to zero and generate sequential reset signals to the BCD counter 90 in synchronism with receipt of speed related signals. As long as the BCD counter continues to be reset, no alarm indication is yielded. However, when the first defect signal is received from the abnormal condition, the reset pulse counter is preset to four and no reset signal is conducted to the BCD counter. The BCD counter then counts to one upon receipt of the first speed related pulse thereafter. The BCD counter will continue to count as long as defect signals are received by the preset pulse counter which is reset by each to the predetermined number four. Assume now that a portion of the unexpected condition is encountered that does not produce defect signals, for example, because of its orientation with respect to the probing ultrasonic energy. The reset pulse counter begins counting down, but as long as it has not counted down to zero it does not generate a reset signal to the BCD counter 90. As long as the reset pulse counter does not count down to zero, that is as long as the interruption of defect signals does not exceed four, or the travel of the transducer does not exceed ¼ inch during such interruption, reset signals will not be sent to the BCD counter 90. When the count of the BCD counters reaches ten, provided that the reset pulse counter has not counted down from four to zero at any point during inspection of the extended abnormal condition, an alarm signal will be generated on line 100 by the binary comparator comparing the count of the BCD counter with that preset in the variable count BCD switches 96.

Accordingly, it will be appreciated that the appratus of the present invention will not arbitrarily fail to detect unacceptable abnormal conditions that for one reason or another fail to produce defect signals during a minimum portion of inspection of them.

The apparatus of the present invention also incorporates a system for yielding an absolute indication of the length of an unacceptable abnormal condition. More particularly, as can be seen in FIG. 4, the alarm signal on line 100 is conducted to the clock input 112 of a flip-flop 114. The Q output from the flip-flop is conducted on line 116 to one input of an AND gate 118. The other input to the AND gate is supplied on line 120 from the speed related pulse generator 78 and line receivers and drivers 80. The D input of the flip-flop 114 is constantly enabled.

Accordingly, when an alarm enable signal is generated on line 100, the flip-flop is clocked to enable the Q output on line 116. Therefore, each time the speed related pulse generator generates one pulse, both inputs to the AND gate 118 are satisfied. Therefore, the output from the AND gate pulsates in synchronism with the speed related pulses.

The clear input 122 to the flip-flop 114 is connected on line 125 to the reset pulse counter through the OR gate 113. Accordingly, when the reset pulse counter counts down to zero to generate a reset pulse indicating that the abnormal condition is no longer being detected, the flip-flop is cleared and the Q output therefrom line 116 becomes disabled. Therefore, the output from the AND gate is disabled an indication of the end of the unacceptable abnormal condition is provided.

The output from AND gate 118 is conducted to an alarm driver and recorder 128 and to a visual alarm indicator 130 that are actuated in synchronism with the AND gate 118 output, that is, as long as the abnormal condition is indicated. These components may take any desired form such as an oscilloscope or may provide an audible indication of alarm or may provide a visual indication by painting the rail where an unacceptable abnormal condition is indicated.

The output from the AND gate 118, from initial generation of the alarm signal through failure to generate an alarm signal, gives an absolute indication of the magnitude of the unacceptable abnormal condition when considered with the predetermined distance set in the variable count BCD switches 96 above which an alarm signal is generated less the preset amount set in the reset counter 104 by the variable present count switches 110. It will be appreciated, then, that the apparatus of the present invention provides substantial improvement over prior art apparatus that merely indicated unacceptable abnormal conditions but did not indicate their magnitude.

The apparatus of the present invention also includes an asynchronous reset switch 132 connected on line 134 to the OR gate 113. Accordingly, an operator may manually reset the BCD counters as desired.

The apparatus of the present invention also includes circuitry for generating a control signal or a distance marker at each interval of a predetermined distance of movement of the ultrasonic transducer relative to the rail. This circuitry includes a "divide-by-N-counter" 136 which in the preferred embodiment is a "divide-by-192-counter". This counter counts each of the speed related pulses on line 84 and generates one pulse for each 192 pulses counted. Since 16 pulses are generated per inch, the counter generates one pulse per foot on line 138 which is conducted to a second pole of the funtion mode select switch 86. Accordingly, the BCD counter will count each of these one pulses per foot and the variable count of BCD switch may be set at one so that an alarm signal is generated on line 100 indictive of each one foot of travel. When the function mode select switch 86, which has ganged lines, is set in position 2 and the reset mode position is set in position A, the generation of an alarm signal on line 100 and consequently on line 146 feeds back to the BCD counter 90 as a reset signal resetting the counter 90 to zero. Accordingly, the BCD counter will not again count to one until generation of a second distance pulse from the "Divide-by-N-counter" 136.

The apparatus of the invention also incorporates a counter bypass switch 140 that when set in position B bypasses the counter circuit to yield indication of an abnormal condition each time a defect signal is generated by the positive and negative gates echo pulse generator 32. It may be desirable to operate in this mode to indicate all detected anomalies in the rail.

It will be appreciated that the present invention as described above in detail, constitutes a substantial improvement over known prior art apparatus. It is designed to detact unacceptable abnormal conditions that nevertheless do not generate defect signals during a portion of the inspection thereof. It further functions to give an absolute indication of the total magnitude of such conditions.

Accordingly, although a specific embodiment of the present invention has been described above in detail, it is to be understood that this is for purposes of illustration. Modification may be made to the described apparatus for inspecting a test piece in order to adapt it to particular applications.

What is claimed is:

1. In an apparatus for inspecting a test piece and indicating an unacceptable condition therein, including means for transmitting a test signal into said test piece, for receiving an associated response signal reflected back thereto, and for generating a defect signal when the character of said response signal indicates an abnormal condition in said test piece; means for moving said transmitting-receiving means relative to said test piece; means for generating a control signal at each of a plurality of predetermined intervals of distance of said movement of said transmitting-receiving means; means for pulsing said transmitting-receiving means to sequentially generate test signals at a frequency independent of generation of said control signals; and principal counter means for counting said controls signals in response to generation of defect signals and being reset to an initial value in response to the absence of generation of defect signals, said principal counter means further producing an alarm signal when it accumulates a count of said control signals that exceeds a preset amount in response to generation of sufficient defect signals during said movement of said transmitting-receiving means over a predetermined distance to confirm the presence of an abnormal condition that is unacceptable; the improvement comprising:

reset counter means connected (1) to said transmitting-receiving means for receiving defect signals therefrom; (2) to said control signal generating means and being reset to an initial amount upon receipt of any one defect signal but counting control signals in the absence of receipt of defect signals and producing a reset signal when the accumulated count equals a predetermined amount indicative of the maximum distance of movement of said transmitting-receiving means during which a defect signal may not be generated from an unacceptable abnormal condition; and (3) to said principal counter means for conducting a reset signal thereto;

whereby said principal counter means is reset by said reset signal when said reset counter accumulates a count equal to said predetermined amount indicating that defect signals have not been generated during movement of said transmitting-receiving means over a distance equal to said maximum distance and whereby said principal counter means accumulates a count of control signals as long as said reset counter receives at least one defect signal before accumulating a count equal to said predetermined amount.

2. The improvement in apparatus for inspecting a test piece according to claim 1, wherein said reset counter means comprises a reset pulse counter which is preset to said predetermined amount each time a defect signal is received; which incrementally counts down from said predetermined amount each time a control signal is received and a defect signal is not received; and which generates one reset signal only when it counts down as aforesaid from said predetermined amount to zero.

3. The improvement in apparatus for inspecting a test piece according to claims 1 or 2, further comprising means connected to said reset counter means for selectably varying said predetermined amount.

4. The improvement in apparatus for inspecting a test piece according to claim 1 or 2, further comprising means for signaling the distance of movement of said transmitting-receiving means, between generation of an alarm signal and resetting of said principal counter means, as a measure of the total length of an unacceptable abnormal condition.

5. The improvement in apparatus for inspecting a test piece according to claim 4, said signaling means comprising flip-flop means activated when one said alarm signal is generated and deactivated when a reset signal is generated by said reset counter means.

6. The improvement in apparatus for inspecting a test piece according to claim 5, wherein said flip-flop means is connected to said reset counter for receiving reset signals therefrom and to said principal counter means for receiving alarm signals therefrom; said signaling means further comprising AND gate means having one input from said flip-flop means and a second input from said control signal generating means and having an output that is enabled by simultaneous receipt of an activated signal from said flip-flop means and a control signal from said control signal generating means at said inputs, and alarm driver means for indicating the presence and absence of an enabled output from said AND gate means.

7. The improvement in apparatus for inspecting a test piece according to claim 1, wherein said transmitting-receiving means comprises at least one ultrasonic transducer.

8. The improvement in apparatus for inspecting a test piece according to claim 7, wherein said moving means comprises at least one test wheel mounted for rolling contact with said test piece in which said ultrasonic transducer is mounted, and a coupling medium carried in said wheel for ultrasonically coupling said transducer to said test piece.

9. The improvement in apparatus for inspecting a test piece according to claim 1, further comprising control-counter means connected to said control signal generating means for counting said control signals, for generating one distance signal each time the count of said control signals thereby indicates a predetermined distance of said movement of said transmitting-receiving means and being reset each time one said distance signal is generated; said distance signals thereby indicating predetermined increments of movement of said transmitting-receiving means.

10. In an apparatus for inspecting a test piece and indicating an unacceptable condition therein, including means for transmitting a test signal into said test piece, for receiving an associated response signal reflected back thereto, and for generating a defect signal when the character of said response signal indicates an abnormal condition in said test piece; means for moving said transmitting-receiving means relative to said test piece; means for generating a control signal at each of a plurality of predetermined intervals of distance of said movement of said transmitting-receiving means; means for pulsing said transmitting-receiving means to sequentially generate test signals at a frequency independent of generation of said control signals, principal counter means for counting said control signals in response to generation of defect signals and being reset to an initial value in response to the absence of generation of defect signals, said principal counter means further producing an alarm signal when it accumulates a count of said control signals that exceeds a preset amount in response to generation of sufficient defect signals during said movement of said transmitting-receiving means over a predetermined distance to confirm the presence of an abnormal condition that is unacceptable; and means for generating a reset signal to said principal counter means based on the absence of defect signals generated by said transmitting-receiving means; the improvement comprising:

means for signaling the distance of movement of said transmitting-receiving means between generation of an alarm signal and resetting of said principal counter means as a measure of the total length of an unacceptable abnormal condition.

11. The improvement in apparatus for inspecting a test piece according to claim 10, said signaling means comprising flip-flop means connected to said principal counter means for receiving alarm signals therefrom and to said reset signal generating means for receiving reset signals therefrom, and being activated when one said alarm signal is generated and deactivated when one said reset signal is generated.

12. The improvement in apparatus for inspecting a test piece according to claim 11, said signaling means further comprising AND gate means having one input from said flip-flop means and a second input from said control signal generating means and having an output that is enabled by simultaneous receipt of an activated signal from said flip-flop means and a control signal from said control signal generating means, and alarm driver means for indicating the present and absence of an enabled output from said AND gate means.

13. The improvement in apparatus for inspecting a test piece according to claims 10 or 11 wherein said reset signal generating means comprises reset counter means connected (1) to said transmitting-receiving means for receiving defect signals therefrom; (2) to said control signal generating means and being reset to an initial amount upon receipt of any one defect signal but counting control signals in the absence of receipt of defect signals and producing a reset signal when the accumulated count equals a predetermined amount indicative of the maximum distance of movement of said transmitting-receiving means during which a defect signal may not be generated from an unacceptable abnormal condition; and (3) to said principal counter means for conducting a reset signal thereto;

whereby said principal counter means is reset by said reset signal when said reset counter accumulates a count equal to said predetermined amount indicating that defect signals have not been generated during movement of said transmitting-receiving means over a distance equal to said maximum distance and whereby said principal counter means accumulates a count of control signal as long as said reset counter receives at least one defect signal before accumulating a count equal to said predetermined amount.

14. The improvement in apparatus for inspecting a test piece according to claim 13, wherein said reset counter means comprises a reset pulse counter which is preset to said predetermined amount each time a defect signal is received; which incrementally counts down from said predetermined amount each time a control signal is received and a defect signal is not received; and which generates one said reset signal only when it counts down as aforesaid from said predetermined amount to zero.

15. The improvement in apparatus for inspecting a test piece according to claim 13, further comprising means connected to said reset counter means for selectably varying said preset amount.

16. The improvement in apparatus for inspecting a test piece, according to claim 10, further comprising control counter means connected to said control signal generating means for counting said control signals, for generating one distance signal each time the count of said control signals thereby indicates a predetermined distance of movement of said transmitting-receiving means, and being reset each time one said distance signal is generated; said distance signals thereby indicating predetermined increments of movement of said transmitting-receiving means.

17. The improvement in apparatus for inspecting a test piece, according to claim 10, 11 or 12 wherein transmitting-receiving means comprises at least one ultrasonic transducer.

18. The improvement in apparatus for inspecting a test piece, according to claim 15 wherein said moving means comprises at least one wheel mounted for rolling contact with said test piece and in which said ultrasonic transducer is mounted, and a coupling medium carried in said wheel for ultrasonically coupling said transducer to said test piece.

19. In an apparatus for inspecting a test piece and indicating an unacceptable condition therein, including means for transmitting a test signal into said test piece, for receiving an associated response signal reflected back thereto, and for generating a defect signal when the character of said response signal indicates an unexpected condition in said test piece; means for moving said transmitting-receiving means relative to said test piece; means for generating a control signal at each of a plurality of predetermined intervals of distance of said movement of said transmitting-receiving means; means for pulsing said transmitting-receiving means to sequentially generate test signals at a frequency independent of generation of said control signals; and principal counter means for counting said control signals in response to generation of defect signals and being reset to an initial value in response to the absence of defect signals, said principal counter means further producing an alarm signal when it accumulates a count of said control signals that exceeds a predetermined amount in response to generation of sufficient defect signals during said movement of said transmitting-receiving means over a predetermined distance to confirm the presence of an abnormal condition that is unacceptable; the improvement comprising:

resetting means for resetting said principal counter means only in the absence of generation of defect signals during movement of said transmitting-receiving means over a distance at least equal to the maximum distance during which a defect signal may not be generated from an unacceptable abnormal condition.

* * * * *

UNITED STATES PATENT AND TRADEMARK OFFICE
CERTIFICATE OF CORRECTION

PATENT NO. : 4,429,576

DATED : February 7, 1984

INVENTOR(S) : JAMES R. NORRIS

It is certified that error appears in the above-identified patent and that said Letters Patent is hereby corrected as shown below:

Col. 1, line 47, between "or" and "abnormal" insert --an--.

Col. 3, line 38, between "to" and "and" insert --detect--; and between "signal" and "abnormal" insert --unacceptable--;

line 67, change "fair" to --fail--.

Col. 4, line 21, change "a" to --an-- (first occurrence);

line 43, change "valve" to --value-- line 68, between "have" and "been" insert --not--.

Col. 5, line 33, change "condition" to --invention--;

line 42, between "minimization" and "unwanted" insert --of--;

line 61, between "transmitting" and "receiving" insert -- - --.

Col. 6, line 10, delete "of" (first occurrence).

Col. 7, line 12, change "homogenious" to --homogeneous--.

Col. 8, line 21, between "also" and "principal" insert --a--;

UNITED STATES PATENT AND TRADEMARK OFFICE
CERTIFICATE OF CORRECTION

PATENT NO. : 4,429,576

DATED : February 7, 1984

INVENTOR(S) : JAMES R. NORRIS

It is certified that error appears in the above-identified patent and that said Letters Patent is hereby corrected as shown below:

Col. 8, line 24, delete "is";

line 25, between "invention" and "to" insert --is--.

Col. 9, line 61, change "treshold" to --threshold--.

Col. 10, line 30, change "and" to --the--;

line 39, change "a" to --an--.

Col. 11, line 38, after "10" change " , " to -- . --.

Col. 12, line 5, change "matter" to --manner--;

line 27, change "expected" to --abnormal--.

Col. 14, line 45, change "an" to --and--;

line 51, between "components" and "may" insert --128 and 130--.

Signed and Sealed this

Twenty-fourth Day of July 1984

[SEAL]

Attest:

GERALD J. MOSSINGHOFF

Attesting Officer

Commissioner of Patents and Trademarks